US009221729B1

(12) United States Patent
Lee

(10) Patent No.: US 9,221,729 B1
(45) Date of Patent: Dec. 29, 2015

(54) EXTRACTIVE DISTILLATION FOR AROMATICS RECOVERY

(71) Applicant: Fu-Ming Lee, Katy, TX (US)

(72) Inventor: Fu-Ming Lee, Katy, TX (US)

(73) Assignee: ALLNEW Chemical Technology Company, Taipei (TW)

( * ) Notice: Subject to any disclaimer, the term of this patent is extended or adjusted under 35 U.S.C. 154(b) by 0 days.

(21) Appl. No.: 14/628,792

(22) Filed: Feb. 23, 2015

(51) Int. Cl.
*C07C 7/08* (2006.01)
*B01D 3/40* (2006.01)
*B01D 3/14* (2006.01)
*B01D 11/04* (2006.01)
*B01D 5/00* (2006.01)
*C07C 15/02* (2006.01)

(52) U.S. Cl.
CPC . *C07C 7/08* (2013.01); *B01D 3/143* (2013.01); *B01D 3/40* (2013.01); *B01D 5/006* (2013.01); *B01D 5/009* (2013.01); *B01D 11/0488* (2013.01); *B01D 11/0492* (2013.01); *C07C 15/02* (2013.01)

(58) Field of Classification Search
CPC ........ B01D 3/40; B01D 5/006; B01D 5/0063; C07C 7/08; C07C 15/00; C07C 15/02; C07C 15/04
See application file for complete search history.

(56) References Cited

U.S. PATENT DOCUMENTS

| 3,026,253 | A | * | 3/1962 | Woerner | C07C 7/08 203/54 |
| 3,544,453 | A | * | 12/1970 | Thompson | B01D 11/0488 208/321 |
| 4,053,369 | A | | 10/1977 | Cines | |
| 5,031,754 | A | * | 7/1991 | Emmrich | C10G 7/08 202/176 |
| 5,215,629 | A | * | 6/1993 | Skatulla | C07C 7/08 203/22 |
| 5,849,982 | A | * | 12/1998 | Lee | B01D 3/322 203/53 |
| 5,877,385 | A | * | 3/1999 | Lee | B01D 3/322 585/435 |
| 6,616,831 | B1 | | 9/2003 | Gentry et al. | |
| 7,078,580 | B2 | | 7/2006 | Tian et al. | |
| 8,246,815 | B2 | * | 8/2012 | Wu | C07C 7/08 208/313 |
| 8,362,314 | B2 | * | 1/2013 | Stabel | B01D 3/40 585/833 |
| 8,378,164 | B2 | * | 2/2013 | Stabel | B01D 3/40 585/833 |
| 9,005,405 | B2 | * | 4/2015 | Wu | B01D 3/40 203/43 |
| 2013/0228447 | A1 | * | 9/2013 | Wu | B01D 3/40 203/28 |
| 2013/0251596 | A1 | * | 9/2013 | Monson | B65G 17/38 422/119 |

OTHER PUBLICATIONS

Fu-Ming Lee et al, "Two Liquid-Phase Extractive Distillation for Aromatics Recovery," Ing. Eng. Chem. Res. (26) No. 3, 564-573, 1987.

\* cited by examiner

*Primary Examiner* — Renee E Robinson
*Assistant Examiner* — Jonathan Miller
(74) *Attorney, Agent, or Firm* — Cascio & Zervas

(57) ABSTRACT

Extractive distillation for recovering aromatic hydrocarbons employs an extractive distillation column with a novel overhead system including a partial condenser. The process enables (i) efficient removal of heavy non-aromatics, particularly $C_8$ naphthenic compounds, from the EDC bottom stream to increase the purity of aromatic products, especially of the mixed xylenes and (ii) reduction (or better control) of benzene loss to the raffinate product stream to maintain its quality as a gasoline blend stock and, as a result, enhance benzene recovery in the aromatic products. Feedstock includes a full-range feedstock, such as pyrolysis gasoline, or a narrow-range feedstock, such as reformate.

19 Claims, 2 Drawing Sheets

EXTRACTIVE DISTILLATION FOR AROMATICS RECOVERY

FIELD OF THE INVENTION

The present invention is directed to techniques for recovering aromatic hydrocarbons from mixtures containing aromatic and non-aromatic hydrocarbons and particularly to methods that employ an extractive distillation column with a novel overhead system.

BACKGROUND OF THE INVENTION

Recovering aromatic hydrocarbons from mixtures containing the aromatic and non-aromatic hydrocarbons (HCs) can be achieved with liquid-liquid extraction (LLE) or extractive distillation (ED). In ED, a nonvolatile polar solvent is added to an extractive distillation column (EDC) to increase the relative volatility between the more-polar and less-polar components that have close-boiling points. In general, the solvent is added to the upper portion of the EDC and a hydrocarbon (HC) feed is introduced to the middle portion of the EDC. As the nonvolatile solvent descends through the column, it preferentially extracts the more-polar components to form a rich solvent that moves toward the bottom of the EDC while the less-polar component vapor ascends to the top. The overhead vapor is condensed and a portion of the condensate is recycled to the top of the EDC as reflux and the other portion of the condensate is withdrawn as raffinate product. The rich solvent containing the solvent and the more-polar components is fed to a solvent recovery column (SRC) to recover (i) the more-polar components as the overhead product and (ii) the lean solvent (free of the feed components) as the bottom product, which is recycled to the upper portion of the EDC. A portion of the overhead product is recycled to the top of the SRC as the reflux to knock down any entrained solvent in the overhead vapor. The SRC is optionally operated under reduced pressure (vacuum) and/or with a stripping medium to lower the column bottom temperature.

ED processes for recovering aromatic HCs are described in U.S. Pat. No. 7,078,580 to Tian et al., U.S. Pat. No. 4,053,369 to Cines, and F. Lee, et al., "Two Liquid-Phase Extractive Distillation for Aromatics Recovery," Ind. Eng. Chem. Res. (26) No. 3, 564-573, 1987.

Although the ED process is simpler to implement than the LLE process, ED has a number of crucial operational limitations. For instance, the ED process is more restricted by the boiling range of the feedstock than is the LLE process. In order to achieve acceptable aromatic HCs purity and recovery, the solvent needs to keep essentially all the benzene (which is the heavy key with the lightest aromatic compound boiling at 80.1° C.) at the EDC bottom thereby driving virtually all of the heaviest non-aromatics into the overhead of the EDC. For a narrow boiling-range ($C_6$-$C_7$) aromatic feedstock, the non-aromatic components (the light key) are the $C_7$ naphthenes, such as ethylcyclopentane (boiling point of 103.5° C.). For a full boiling-range ($C_6$-$C_8$) aromatic feedstock, the non-aromatic components (the light key) are the $C_8$ naphthenes, such as ethylcyclohexane (boiling point of 131.8° C.). These compounds become the light key components not only because of their higher boiling points but also because of their stronger tendency to stay with the solvent and aromatic compounds due to their higher polarity as compared to other non-aromatic compounds in the feed. It is much more difficult to recover benzene, toluene and xylenes (BTX) aromatics from the full boiling-range feedstock, such as the full range pyrolysis gasoline, than to recover benzene and toluene from the narrow boiling-range feedstock, such as the $C_6$-$C_7$ reformate. However, even a well defined narrow boiling-range feedstock contains at least two percent of $C_8$ hydrocarbons including $C_8$ aromatics and naphthenes.

SUMMARY OF THE INVENTION

It has been shown that in prior art ED processes, the level of naphthenic impurities in the $C_8$ aromatic product is noticeably higher than that produced by the LLE process. High concentrations of $C_8^+$ naphthenic impurities can cause significant problems in the subsequent xylene isomerization and purification units in p-xylene production. This presents a challenge to ED technology, especially for the BTX aromatics production from a full-range ($C_6$-$C_8$) feedstock. The present invention recognizes the importance of reducing the naphthenes content in the aromatics product, especially in $C_8$ aromatics.

The present invention provides a novel EDC configuration and attendant operations to significantly improve the removal of heavy non-aromatics, especially the $C_8$ naphthenic compounds, from the EDC bottom solvent-rich stream in order to enhance the purity of aromatic products, especially of $C_8$ aromatic HCs. The inventive aromatic recovery process reduces (or controls) benzene loss to the EDC overhead raffinate (non-aromatic) product stream so as to maintain its quality as a suitable gasoline blend stock and thus increase recovery of benzene in the aromatic product. The efficiency of the lower section of the modified EDC is superior to conventional EDCs. The invention is based, in part, on the recognition improved aromatics recovery can be achieved by adding a solvent-rich stream to the overhead system to extract benzene in the EDC overhead raffinate stream, recycling the solvent phase to the lower portion of the EDC, and withdrawing the hydrocarbon phase as the overhead product after traces of solvent are removed.

In conventional EDC operations, benzene is essentially the only aromatic HC that is lost to the EDC overhead raffinate stream due to its low boiling point. With the present ED process, benzene in the EDC overhead raffinate stream is extracted by a solvent-rich stream and recycled to a lower portion of the EDC, so more heavy non-aromatic HCs, especially $C_8$ naphthenes, is driven to the EDC overhead without concern with the loss of benzene from the aromatic product stream that is withdrawn from the bottom of the EDC.

Therefore, the present invention provides an improved EDC operation for the ED process to recover benzene, toluene and xylenes and $C_8$ aromatic HCs from a full-range feedstock, such as pyrolysis gasoline, or from a narrow-range feedstock, such as reformate. The amount of heavy non-aromatic HCs, especially $C_8$ naphthenes, in the aromatic products is significantly reduced thereby enhancing the purity of the mixed xylenes to levels comparable to those produced by the LLE process.

In one aspect, the invention is directed to an ED process with improved configurations and operations in the EDC for recovering aromatic HCs with reduced non-aromatic HC contaminants, and increased benzene recovery from a HC feed mixture comprising aromatic and non-aromatic HCs, which process includes the steps of:

(a) introducing a feed containing aromatic and non-aromatic HCs into a middle portion of an EDC and introducing a first solvent-rich stream containing essentially the solvent and water into an upper portion of the EDC as a selective solvent feed;

(b) withdrawing a non-aromatic HCs-rich stream containing water, non-aromatic HCs, benzene, and trace of other aromatic HCs from a top of the EDC and recovering a second solvent-rich stream containing the solvent, aromatic HCs and trace of non-aromatic HCs from a bottom of the EDC;

(c) mixing a third solvent-rich stream having the same composition as the first solvent-rich stream, with said non-aromatic HCs-rich stream in step (b) to generate a solvent phase and a raffinate phase.

(d) recycling the solvent phase in step (c) containing, benzene, water, and trace of other aromatic HCs to a lower portion of the EDC.

(e) withdrawing at least a portion of the raffinate phase in step (c) as the raffinate product after water washing to remove trace of the solvent; and recycling the other portion to a top of the EDC as a reflux.

(f) introducing the second solvent-rich stream in step (b) into a middle portion of a solvent recovery column (SRC), recovering an aromatic HCs-rich stream, that is substantially free of solvent and non-aromatic HCs, from a top of the SRC, and removing a fourth solvent-rich stream containing essentially the solvent and water from a bottom of the SRC;

(g) introducing a major portion of said fourth solvent-rich stream (first solvent-rich stream) into an upper portion of the EDC in step (a) as a selective solvent feed; mixing a minor portion of said fourth solvent-rich stream (third solvent-rich stream) with said non-aromatic HCs-rich stream in step (b); and introducing another minor portion of said fourth solvent-rich stream (fifth solvent-rich stream) into an upper portion of a thermal solvent regeneration zone, removing heavy sludge from a lower portion of the solvent regeneration zone, and recovering a sixth solvent-rich stream containing solvent, water, and hydrocarbons and other compounds having boiling points below that of the solvent, from a top of the solvent regeneration zone for recycling to a lower portion of the SRC in step (f).

In another aspect, this invention is directed to an ED process with improved configurations and operations in the EDC for recovering aromatic HCs with reduced non-aromatic HC contaminants, and increased benzene recovery from a hydrocarbon HC feed mixture of aromatic and non-aromatic HCs, which process includes the steps of:

(a) introducing a feed containing aromatic and non-aromatic HCs into a middle portion of an EDC and introducing a first solvent-rich stream containing essentially the solvent and water into an upper portion of the EDC as a selective solvent feed;

(b) withdrawing a non-aromatic HCs-rich stream containing water, non-aromatic HCs, benzene, and trace of other aromatic HCs from a top of the EDC and recovering a second solvent-rich stream containing the solvent and aromatic HCs from a bottom of the EDC;

(c) partially condensing a non-aromatic HCs-rich stream from a top of the EDC in step (b) to partially remove water and heavier HCs to form a water and heavier HCs reduced non-aromatic HCs-rich stream;

(d) mixing a third solvent-rich stream having the same composition as said first solvent-rich stream, with the water and heavier HCs reduced non-aromatic HCs-rich stream in step (c) and introducing the mixture to an EDC overhead system to generate a solvent phase and a raffinate phase.

(e) recycling the solvent phase in step (d) containing, benzene, water, and trace of other aromatic HCs to a lower portion of the EDC.

(f) withdrawing at least a portion of the raffinate phase in step (d) as the raffinate product after water washing to remove trace of the solvent; and recycling the other portion to a top of the EDC as a reflux.

(g) introducing the second solvent-rich stream in step (b) into a middle portion of a solvent recovery column (SRC), recovering an aromatic HCs-rich stream, that is substantially free of solvent and non-aromatic HCs, from a top of the SRC, and removing a fourth solvent-rich stream containing essentially the solvent and water from a bottom of the SRC;

(h) introducing a major portion of said fourth solvent-rich stream (first solvent-rich stream) into an upper portion of the EDC in step (a) as a selective solvent feed; mixing a minor portion of said fourth solvent-rich stream (third solvent-rich stream) with the water and heavier HCs reduced non-aromatic HCs-rich stream in step (c); and introducing another minor portion of said fourth solvent-rich stream (fifth solvent-rich stream) into an upper portion of a thermal solvent regeneration zone, removing heavy sludge from a lower portion of the solvent regeneration zone, and recovering a sixth solvent-rich stream containing solvent, water, and HCs and other compounds having boiling points below that of the solvent, from a top of the solvent regeneration zone for recycling to a lower portion of the SRC in step (g).

DETAILED DESCRIPTION OF PREFERRED EMBODIMENTS

Figure 1:
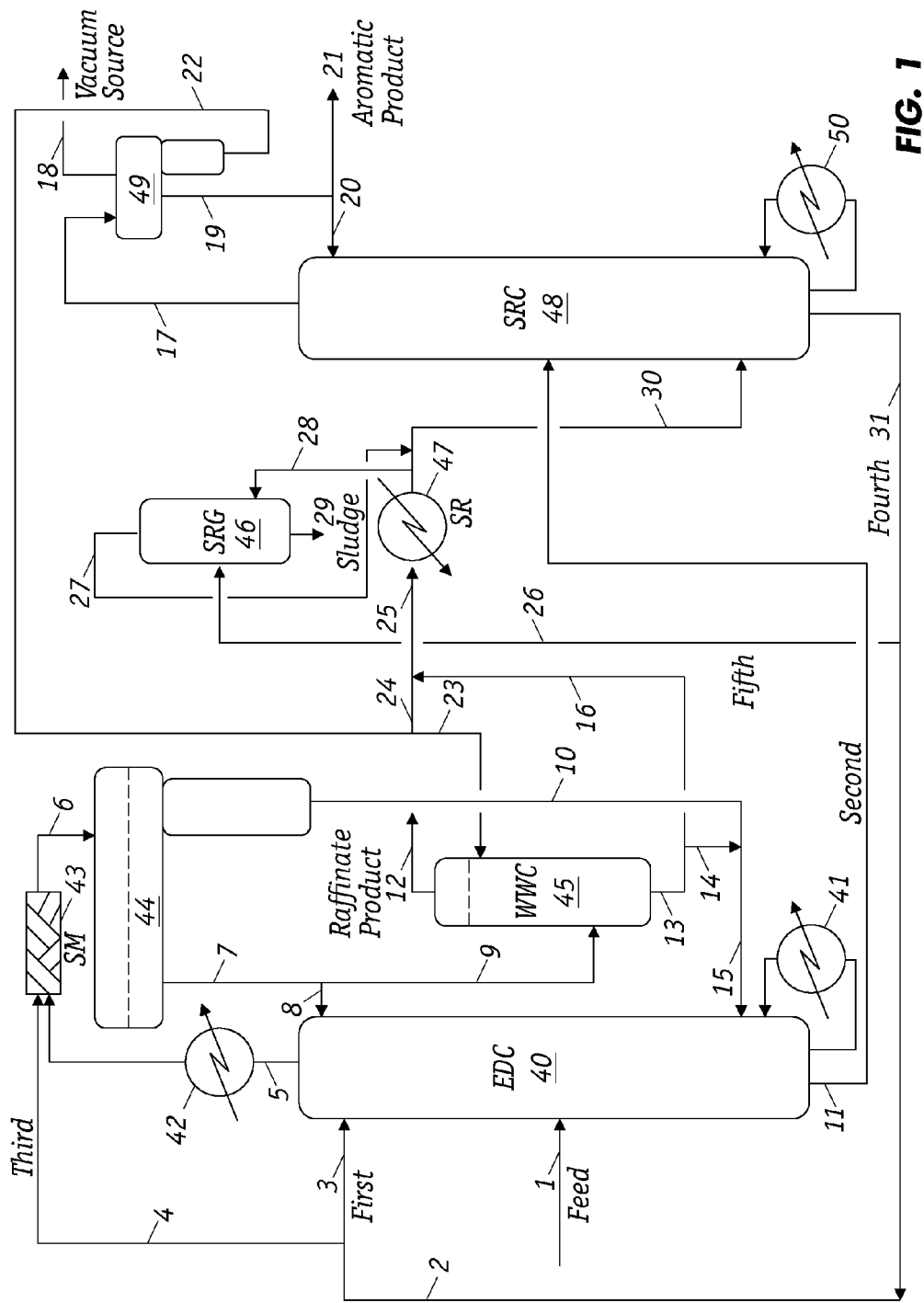
FIG. 1 illustrates a process for extracting benzene from the EDC overhead raffinate stream in an in-line static mixer, allowing increased removal of heavy naphthenes from the EDC bottom solvent-rich stream for improving $C_8$ aromatic purity and benzene recovery.

Testing results on full-range feedstock demonstrate that with prior art ED processes the content of non-aromatic HCs (consisting mostly $C_8$ naphthenic HCs) in the aromatic extract product is in the range of 0.4 to 0.7 wt % thereby generating a $C_8$ aromatic product with purity below 98.5 wt % (which is a minimum purity requirement). In contrast, with similar feedstock, LLE processes yield an extract product with less than 0.1 wt % non-aromatic HCs.

It is generally recognized that the solubility of hydrocarbons in sulfolane or other polar solvent is in sequence of: Aromatics>>Naphthenes>Olefins>Paraffins. In other words, the solubility of aromatics is significantly higher than that of naphthenes. Therefore, a feature of the present invention for reducing naphthenic HCs in aromatic product is to incorporate a secondary solvent to the EDC overhead stream to preferentially extract benzene and other aromatic components in the stream to form a solvent phase, leaving most of the naphthenes and other less polar non-aromatic components in the raffinate phase to be withdrawn as the raffinate product after a water wash to remove traces of solvent.

The solvent phase is then recycled to the EDC to recover mainly benzene and minor amounts of other aromatic compounds. This adaptation allows the EDC reboiler to drive more, if not all, of the heavy non-aromatics, especially $C_8$ naphthenes (the light key component) to the EDC overhead, without concerned with loss of benzene (the heavy key component) from the EDC bottom rich solvent stream. Indeed, benzene recovery is improved and controlled since most benzene loss to the EDC overhead is recovered by recycling the benzene extracted with the secondary solvent.

Normally, the water content is controlled in the lean solvent which is fed to near the top of the EDC. As the high-boiling (non-volatile) solvent flowing down the EDC, low-boiling water in the lean solvent is vaporized and raised to the top of the EDC. Therefore, water content in the solvent is highest at the top and lowest at the bottom of the column. Since water is an anti-solvent, this means that the solvent mixture at the top has the lowest solubility (highest selectivity) and the top is where the less soluble non-aromatic HCs are concentrated. Conversely, the solvent mixture at the bottom has the highest solubility (lowest selectivity) and the bottom is where the highly soluble aromatic HCs are present. This water concentration profile is very undesirable.

Since less soluble non-aromatic HCs are concentrated in the upper portion of the EDC, the undesired two liquid phases are present in the upper portion of the EDC when ED solvent such as sulfolane is used. Co-solvent such as water can be beneficial or detrimental to the selectivity of the ED solvent such as sulfolane. Under a single liquid phase, selectivity of sulfolane solvent is significantly enhanced as its water content increased from 0 to 5 wt %. However, the reverse is true when two liquid phases are present. Therefore, selection of the location in EDC to recycle the solvent phase is important to the EDC operation, especially when this solvent phase contains more water than the solvent feed (water in solvent feed plus at least a part of water in the EDC overhead). With the present invention, the EDC overhead stream and the secondary solvent can be mixed in a static mixer or in a multi-stage contactor such as multi-stage mixer/settler.

It is conceivable that adding solvent containing more water to the lower portion of EDC will reverse the undesirable water concentration profile in the EDC. This should lead to better column performance with a reduction in the $C_8^+$ naphthenic content in the aromatic product that is withdrawn from the bottom of the EDC.

FIG. 1 depicts an aromatics recovery process that employs an extractive distillation column (EDC) 40, solvent recovery column (SRC) 48, thermal solvent regenerator (SRG) 46, water wash column (WWC) 45 and inline static mixer (SM) 43. Alternatively, instead of the SM, a multi-stage contactor can be employed. A full-range HC feedstock or a narrow-range HC feedstock is fed via line 1 to the middle portion of EDC 40. The full-range feedstock comprises $C_6$-$C_8$ aromatics including benzene, toluene, ethylbenzene and xylenes, and $C_6$-$C_8$ non-aromatics including paraffins, naphthenes and olefins. The narrow-range feedstock comprises $C_6$-$C_7$ aromatics including benzene, toluene and less than 2% $C_8$ aromatic HCs, and $C_6$-$C_7$ non-aromatic HCs comprising paraffins, naphthenes, and olefins. A major portion of the fourth solvent-rich stream (the first solvent-rich stream) from the bottom of SRC 48 is fed via lines 31, 2 and 3 to near the top of EDC 40 below the overhead reflux entry point for line 8. Typically, 50 to 95 wt % and preferably 90 to 95 wt % of the fourth solvent-rich stream is diverted. The first solvent-rich stream, which enters the EDC, contains an extractive distillation solvent which comprises sulfolane, alkyl-sulfolane, N-formyl morpholine, N-methyl pyrrolidone, tetraethylene glycol, triethylene glycol, diethylene glycol, and mixtures thereof, and preferably with water as the co-solvent. The preferred solvent is sulfolane with up to 5 wt % water and preferably up to 1 wt % water.

The EDC reboiler 41 is operated to drive essentially all of the $C_8$ naphthenes from the second solvent-rich stream from the EDC bottom, without being restricted by the benzene loss from the second-rich stream. The amount of first solvent-rich stream added to the top of the EDC and the EDC reboiler temperature are adjusted to control the benzene content in the EDC overhead raffinate stream in the range of 0 to 10 wt % and preferably 0 to 5 wt %.

Non-aromatics vapor exiting the top of EDC 40 through line 5 is condensed in condenser 42 and the condensate is fed to SM 43 to mix with a third solvent-rich stream having the same composition as the first solvent-rich solvent from line 4. The mixture from SM 43 is fed via line 6 to an overhead receiver 44, which serves to effect a phase separation between the raffinate (non-aromatic HCs) and the solvent phases, wherein the benzene content in the raffinate phase is preferably in the range of 0.1 to 1.0 wt %.

A portion of the raffinate phase is recycled to the top of EDC 40 as reflux via lines 7 and 8 and a second portion is transferred to a lower portion of WWC 45 through lines 7 and 9. Since the stream in line 8 contains increased amounts of $C_8$ naphthenes, the reflux ratio should be minimized to 0.25 or less so as to avoid introducing excess $C_8$ naphthenes into EDC 40. Water is withdrawn from SRC overhead receiver 49 via lines 22 and 23, and is fed to an upper portion of WWC 45, to counter-currently contact with the raffinate stream from receiver 44 in line 9 for removing any trace amount of solvent. Solvent-free raffinate product is then withdrawn from the top of WWC 45 via line 12. The benzene level in the raffinate product is typically 0.1 to 1.0 wt %. A water phase from WWC 45 containing traces of solvent is transferred from the bottom via lines 13 and 16, and combined with the water from receiver 49 through lines 22 and 24. The combined stream is fed to a steam generator (SR) 47 via line 25 to generate stripping steam that is then fed to a lower portion of SRC 48 through line 30.

A solvent phase is withdrawn from receiver 44 via line 10 and combined with a water make-up stream 14, if required, to form a mixed stream in line 15 which is recycled to the single liquid phase region in a lower portion of the EDC 40 to recover the extracted benzene and provide additional solvent for enhancing the EDC operation. The $C_8$ naphthenes content in the rich solvent from the bottom of EDC 40 is reduced not only by the presence of additional solvent, but also by the higher solvent water content in the single liquid phase region which promotes solvent selectivity.

A second rich-solvent consisting of solvent, aromatic HCs, and reduced amounts of non-aromatic HCs (mainly $C_8^+$ naphthenes) is withdrawn from the bottom of EDC 40 and transferred to the middle portion of SRC 48, which is equipped with reboiler 50, via line 11. The volume ratio between the first solvent-rich stream and the HC feedstock steam varies in the range of 1.0 to 5.0 and preferably 2.0 to 4.0. This ratio is adjusting along with the EDC reboiler temperature in order to control the concentration of the $C_8^+$ naphthenes in the second solvent-rich stream to be within the range 0.1 to 1.0 wt % and preferably 0.1 to 0.5 wt %, after being stripped of solvent in SRC 48. The second solvent-rich stream is transferred to the middle portion of SRC via line 11. Stripping steam is injected from steam generator SR 47 via line 30 into the lower portion of SRC 48 to assist in removing the aromatic HCs from the solvent. An aromatic concentrate, containing water and being substantially free of solvent and typically having no more than 1.0 wt % and preferably no more than 0.5 wt % $C_8$ naphthenes and other non-aromatic HCs, is withdrawn as an overhead vapor stream from SRC 48 and introduced into an overhead receiver 49 via line 17 after being condensed in a condenser (not shown). In order to minimize the bottom temperature of SRC 48, overhead receiver 49 is connected to a vacuum source via line 18 to generate sub-atmospheric conditions in SRC 48.

Overhead receiver 49 serves to effect a phase separation between the aromatic HCs and the water phases. A portion of the aromatic HC phase in line 19 is recycled to the top of SRC 48 as reflux via line 20, while the remaining portion is withdrawn as aromatic HC product with reduced $C_8$ naphthenes through line 21. A part of water phase that accumulates in the water leg of overhead receiver 49 is fed via lines 22, 24 and 25 to steam generator SR 47 to produce stripping steam for SRC 48. The other part of water phase is introduced to an upper portion of WWC 45 via lines 22 and 23 to remove the trace of solvent from receiver 44 raffinate stream and produce a solvent-free raffinate stream containing less than 1 wt % benzene via line 12 suitable for gasoline blending.

A major portion of the fourth solvent-rich stream (the first solvent-rich stream) from the bottom of SRC is recycled via lines 31, 2 and 3 to upper portion of EDC 40 for extracting the aromatic HCs. Typically 50 to 95 wt % and preferably 90 to 95 wt % of the fourth solvent-rich stream is diverted to form line 3. A minor portion of the fourth solvent-rich stream (the third solvent-rich stream) is fed via line 4 to inline SM 43 to extract benzene and minor amount of other aromatics. Typically 1 to 10 wt % and preferably 1 to 5 wt % of the fourth solvent-rich stream is diverted to form line 4. A split stream of the fourth solvent-rich stream (the fifth solvent-rich stream) from SRC 48 bottom is diverted into SRG 46 via line 26 and steam is introduced into SRG 48 through line 28, at a location below the lean solvent feed entry point. Typically 1 to 5 wt % of the fourth solvent-rich stream is diverted to form line 26. Deteriorated solvent and polymeric sludge are removed as a bottom stream of SRG 46 through line 29, while the regenerated solvent and substantially all the stripping steam, are recovered as an overhead stream 27 and recycled to the lower portion of SRC 48 via line 30.

In an application of the ED process of FIG. 1 with sulfolane as the solvent, EDC 40 is operated at a solvent-to-HC feed volume ratio of 1.0 to 5.0, preferably 2.0 to 4.0, depending upon the boiling range of the HC feedstock, to allow 0 to 10 wt %, preferably 0 to 5 wt % benzene in the EDC overhead raffinate stream by adjusting the reboiler temperature and the solvent-to-HC feed volume ratio. In extracting the benzene in the EDC overhead raffinate stream, the ratio of the third solvent-rich stream in line 4 to the first solvent-rich stream in line 3 is in the range of 0.1 to 1.0 and preferably 0.01 to 0.1. The water content in the recycled solvent stream in line 15 is in the range of 5 to 25 wt %, depending upon the ratio of the third solvent-rich stream to the first solvent-rich stream.

The temperature of the overhead vapor from SRG 46 typically ranges from 150° to 200° C., and preferably from 160° to 180° C., under a pressure of 0.1 to 10 atmospheres, and preferably of 0.1 to 0.8 atm. SRC 48 is typically operated with stripping steam at a reboiler temperature in the range of 170° to 185° C. under a reduced pressure in the range of 0.4-0.7 atmospheric pressure. Higher temperatures would cause accelerated thermal decomposition of sulfolane (hourly decomposition rate is 0.001 to 0.1% when temperatures exceed 200° C.).

Figure 2:
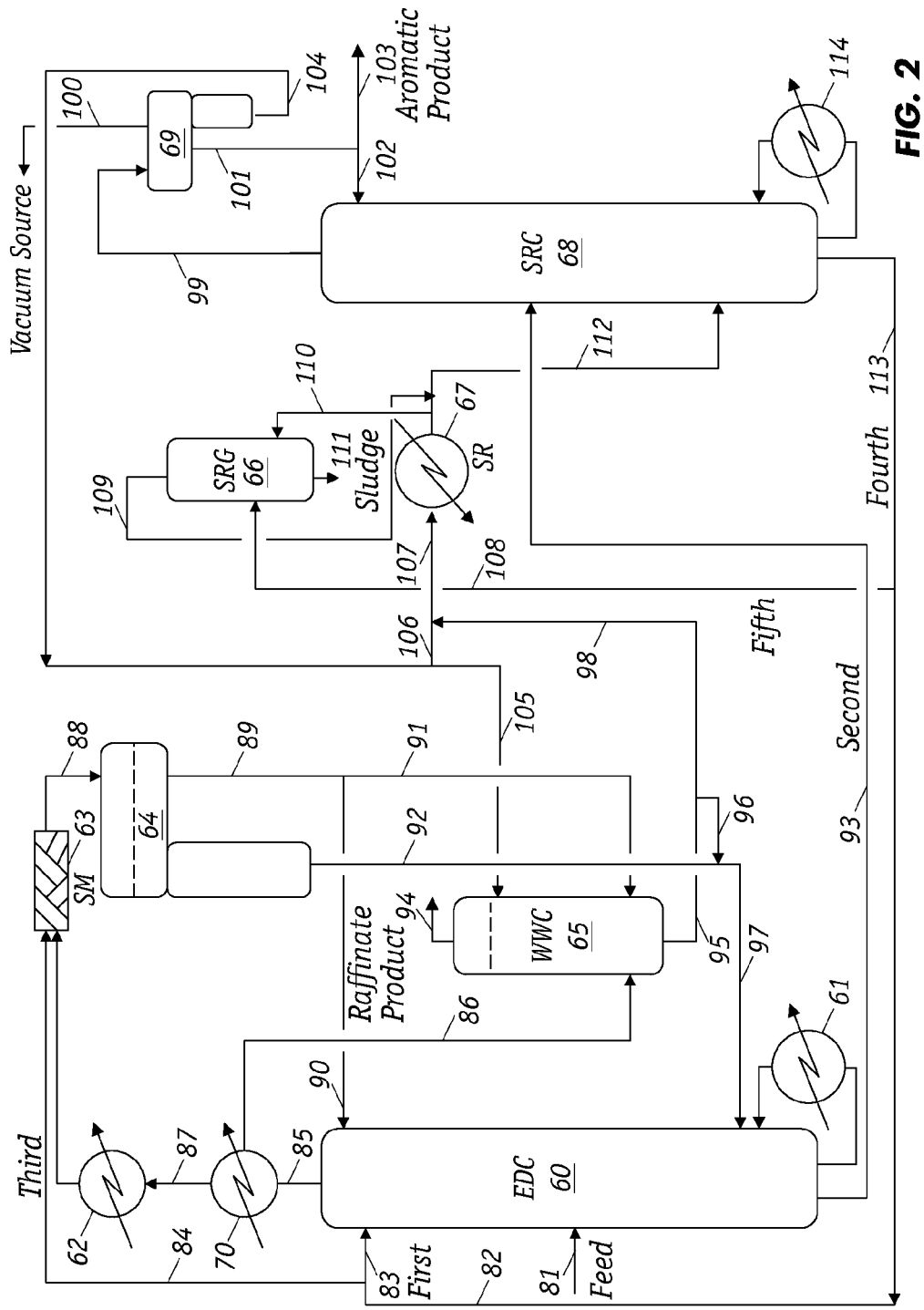
FIG. 2 illustrates a process for extracting benzene from the EDC overhead raffinate stream with reduced water content in the solvent in an in-line static mixer, allowing increased removal of heavy naphthenes from the EDC bottom solvent-rich stream for improving $C_8$ aromatic purity and benzene recovery.

FIG. 2 depicts another aromatics recovery process that employs an extractive distillation column (EDC) 60, solvent recovery column (SRC) 68, thermal solvent regenerator (SRG) 66, water wash column (WWC) 65 and inline static mixer (SM) 63. The flow scheme also incorporates a partial condenser 70 that removes a part of water and heavier non-aromatic HCs, especially $C_8$ naphthenes from the EDC 60 overhead raffinate stream. This process can accommodate the same feed mixtures and use the same solvents as employed with the scheme of FIG. 1.

As a co-solvent, the presence of water strongly affects solvent selectivity and solvency and thus water influences the effectiveness of benzene extraction in inline static mixer SM 63. The addition of partial condenser 70 also reduces the amount of heavier non-aromatic HCs, especially $C_8$ naphthenes, in the reflux in line 90. This improves the performance of the upper portion of EDC 60 where two liquid phases exist and assists in the removal of $C_8$ naphthenes from the EDC 60 bottom aromatic product.

Referring to FIG. 2, an HC feedstock is fed via line 81 to the middle portion of EDC 60, while a major portion of the fourth solvent-rich stream (the first solvent-rich stream) from the bottom of SRC 68, which is equipped with reboiler 114, is fed as the solvent feed via lines 113, 82 and 83 to near the top of EDC 60 below the overhead reflux entry point for line 90. Typically, 50 to 95 wt % and preferably 90 to 95 wt % of the fourth solvent-rich stream is diverted to form line 83. EDC reboiler 61 is operated to drive essentially all the $C_8$ naphthenes from the second solvent-rich stream from the EDC 60 bottom, without being restricted by the benzene loss from the second solvent-rich stream. The amount of first solvent-rich stream introduced to the top of EDC 60 and the reboiler temperature are adjusted in order to control the benzene content in the EDC 60 overhead raffinate stream to be within the range of 0 to 10 wt % and preferably 0 to 5 wt %.

Non-aromatics vapor exiting the top of EDC 60 through line 85 is partially condensed in a partial condenser 70 and the condensate containing mainly water and heavier non-aromatic HCs, especially $C_8$ naphthenes, is fed to a lower portion WWC 65 via line 86. Uncondensed vapor from partial condenser 70 containing mainly benzene, lighter non-aromatic HCs, and having a lowered water content is introduced to a total condenser 62 through line 87, and the condensate is fed to SM 63 to mix with a third solvent-rich stream (a split stream from the first solvent-rich solvent) from line 84. Typically 1 to 10 wt % and preferably 1 to 5 wt % of the fourth solvent-rich stream is diverted to form line 84. Instead of SM 63, a multi-stage contactor can be employed. The mixture from SM 63 is transferred to an overhead receiver 64 via line 88, which serves to effect a phase separation between the raffinate (non-aromatic HCs) and the solvent phases, wherein the benzene level in the raffinate phase should be in the range of 0.1 to 1.0 wt %.

A portion of the raffinate phase is recycled to the top of EDC 60 as reflux via lines 89 and 90 and a second portion is transferred to a lower portion of WWC 65 through lines 89 and 91. Water is withdrawn from SRC overhead receiver 69 via lines 104 and 105 and is fed to an upper portion of WWC 65. The water counter-currently contacts the raffinate stream from overhead receiver 64 in line 91 and the condensate from partial condenser 70 in line 86 to remove trace amounts of solvent and produce a solvent-free raffinate stream containing less than 1 wt % benzene via line 94 which is suitable for gasoline blending. A water phase containing traces of solvent from WWC 65 is transferred from the bottom via lines 95 and 98, and combined with the water from overhead receiver 69 through lines 104 and 106. The combined stream is fed to a steam generator SR 67 via line 107 to generate stripping steam to be fed to a lower portion of SRC 68 through line 112.

A solvent phase is withdrawn from overhead receiver 64 via line 92 and combined with a water make-up stream 96, if required, to form a mixed stream in line 97 which is recycled to the single liquid phase region in a lower portion of the EDC 60 to recover the extracted benzene and provide additional solvent for enhancing the EDC 60 operation.

In an application of the ED process of FIG. 2 with sulfolane as the solvent, EDC 60 is operated at a solvent-to-HC feed volume ratio of 1.0 to 5.0 and preferably 2.0 to 4.0, depending upon the boiling range of the HC feedstock. The process yields 0 to 10 wt % and preferably 0 to 5 wt % benzene in the EDC overhead raffinate stream 85 by adjusting the reboiler 61 temperature and the solvent-to-HC feed volume ratio. The EDC operations simultaneously controls the concentration of $C_8$ naphthenes in the second solvent-rich stream from the bottom of EDC 60 for generating an aromatic concentrate containing 0.1 to 1.0 wt % and preferably 0.1 to 0.5 wt % $C_8$ naphthenes. In extracting the benzene in EDC overhead raffinate stream 85, the ratio of the third solvent-rich stream in line 84 to the first solvent-rich stream in line 83 is preferably in the range of 0.01 to 0.1. The partial overhead condenser 70 removes at least a part of the water in EDC overhead raffinate stream 85. The water content in the recycled solvent stream in line 97 is reduced and controlled at a preferred range of 1 to 5 wt %, depending upon operating condition of partial condenser 70 as well as the ratio of the third solvent-rich stream to the first solvent-rich stream. The ratio of the third solvent-rich stream to first solvent-rich stream is typically ranges from 0.01 to 1 and preferably from 0.01 to 0.1.

In this integrated configuration of FIG. 2, the solvent recovery column, water washing column, solvent regenerator generally operate in the same manner as their corresponding unit operations in the scheme shown in FIG. 1. As a corollary, SRG 66 and attendants lines 109, 110 and 111 operate in the same manner as SRG 46 and lines 27, 28 and 29 of FIG. 1, respectively. Similarly, overhead receiver 69 and attendant lines 99, 100, 101, 102, 103 and 104 operate in the same manner as overhead receiver 49 and attendant lines 17, 18, 19, 20, 21, and 22 of FIG. 1, respectively.

What is claimed is:

1. A process for recovering aromatic hydrocarbons from a hydrocarbon feed mixture comprising a (i) full-range feedstock that includes $C_6$-$C_8$ aromatic hydrocarbons comprising benzene, toluene, ethylbenzene and xylenes and $C_6$-$C_8$ non-aromatic hydrocarbons comprising paraffins, naphthenes and olefins or (ii) a narrow-range feedstock that includes $C_6$-$C_7$ aromatic hydrocarbons comprising benzene, toluene and less than 2% $C_8$ aromatic hydrocarbons and $C_6$-$C_7$ non-aromatic comprising paraffins, naphthenes, and olefins which process comprises the steps of:

(a) introducing a feed containing aromatic and non-aromatic hydrocarbons (HCs) into a middle portion of an extractive distillation column (EDC) and introducing a first solvent-rich stream comprising an extractive distillation solvent and water into an upper portion of the EDC;

(b) withdrawing a non-aromatic HC-rich stream from a top of the EDC and recovering a second solvent-rich stream from a bottom of the EDC;

(c) mixing a third solvent-rich stream with the non-aromatic HC-rich stream in a static mixer or a multi-stage contactor to form a mixture that is introduced into a separator vessel where the mixture separates into a solvent phase and a raffinate phase;

(d) recycling the solvent phase, which contains benzene, to a lower portion of the EDC;

(e) washing a first portion of the raffinate to yield a raffinate product and recycling a second portion of the raffinate to a top of the EDC as a reflux;

(f) introducing the second solvent-rich stream into a middle portion of a solvent recovery column (SRC), recovering an aromatic HC-rich stream from a top of the SRC, and removing a fourth solvent-rich stream from a bottom of the SRC;

(g) diverting a major portion of the fourth solvent-rich stream from the bottom the SRC as the first solvent-rich stream that is introduced into an upper portion of the EDC, diverting a first minor portion of the fourth solvent-rich stream as the third solvent-rich stream which is mixed with the non-aromatic HC-rich stream in step (b), and diverting a second minor portion of the fourth solvent-rich stream as a fifth solvent-rich stream which is introduced into an upper portion of a thermal solvent regeneration zone; and (h) removing sludge from a lower portion of the thermal solvent regeneration zone and recovering a sixth solvent-rich stream from a top of the thermal solvent regeneration zone and recycling the sixth solvent-rich stream to a lower portion of the SRC.

2. The process of claim 1 wherein the feed mixture comprises the full-range feedstock.

3. The process of claim 1 wherein the first solvent-rich stream comprises a solvent that is selected from the group consisting of sulfolane, alkyl-sulfolane, N-formyl morpholine, N-methyl pyrrolidone, tetraethylene glycol, triethylene glycol, diethylene glycol, and mixtures thereof and water as co-solvent.

4. The process of claim 3 wherein the first solvent-rich stream comprises sulfolane with water as co-solvent.

5. The process of claim 1 wherein the third solvent-rich stream and the non-aromatic HC-rich stream are mixed in a static mixer.

6. The process of claim 1 wherein the non-aromatic HC-rich stream contains water, non-aromatic HCs, benzene and trace amounts of other aromatic HCs.

7. The process of claim 1 wherein the third solvent-rich stream has the same composition as that of the first solvent-rich stream.

8. The process of claim 1 wherein the solvent phase in step (c) contains solvent, benzene, water, and trace amounts of aromatic HCs.

9. The process of claim 1 wherein the washing the first portion of the raffinate removes solvent.

10. A process for recovering aromatic hydrocarbons from a hydrocarbon feed mixture comprising a (i) full-range feedstock that includes $C_6$-$C_8$ aromatic hydrocarbons (HCs) comprising benzene, toluene, ethylbenzene and xylenes and $C_6$-$C_8$ non-aromatic hydrocarbons comprising paraffins, naphthenes and olefins or (ii) a narrow-range feedstock that includes $C_6$-$C_7$ aromatic hydrocarbons comprising benzene, toluene and less than 2% $C_8$ aromatic hydrocarbons and $C_6$-$C_7$ non-aromatic comprising paraffins, naphthenes, and olefins which comprises the steps of:

(a) introducing a feed containing aromatic and non-aromatic HCs into a middle portion of an extractive distillation column (EDC) and introducing a first solvent-rich stream comprising an extractive distillation solvent and water into an upper portion of the EDC;

(b) withdrawing a non-aromatic HC-rich vapor stream from a top of the EDC and recovering a second solvent-rich stream from a bottom of the EDC;

(c) partially condensing the non-aromatic HC-rich vapor stream to partially remove water and $C_8$ naphthenes to yield a liquid stream and a second vapor stream which is subsequently totally condensed to form a condensate stream;

(d) mixing a third solvent-rich stream with the condensate of second vapor stream in a static mixer or multi-stage contactor to form a mixture that is introduced into a separator vessel where the mixture separates into a solvent phase and a raffinate phase;

(e) recycling the solvent phase, which contains benzene, to a lower portion of the EDC;
(f) washing a first portion of the raffinate phase to yield a raffinate product and recycling a second portion to a top of the EDC as a reflux;
(g) introducing the second solvent-rich stream into a middle portion of a solvent recovery column (SRC), recovering an aromatic HC-rich stream from a top of the SRC, and removing a fourth solvent-rich stream from a bottom of the SRC;
(h) diverting a major portion of the fourth solvent-rich stream from the bottom of the SRC as the first solvent rich stream into an upper portion of the EDC, diving a first minor portion of the fourth solvent-rich stream as the third solvent-rich stream which is mixed with the condensate stream, and diverting a second minor portion of the fourth solvent-rich stream as a fifth solvent-rich stream which is introduced into an upper portion of a thermal solvent regeneration zone; and
(i) removing sludge from a lower portion of the solvent regeneration zone, and recovering a sixth solvent-rich stream from a top of the solvent regeneration zone for recycling to a lower portion of the SRC.

11. The process of claim 10 wherein the feed mixture comprises the full-range feedstock.

12. The process of claim 10 wherein the first solvent-rich stream comprises a solvent that is selected from the group consisting of sulfolane, alkyl-sulfolane, N-formyl morpholine, N-methyl pyrrolidone, tetraethylene glycol, triethylene glycol, diethylene glycol, and mixtures thereof and water as co-solvent.

13. The process of claim 12 wherein the first solvent-rich stream comprises sulfolane with water as co-solvent.

14. The process of claim 10 wherein the third solvent-rich stream and the condensate stream are mixed in a static mixer.

15. The process of claim 10 wherein the non-aromatic HC-rich stream contains water, non-aromatic HCs, benzene and trace amounts of other aromatic HCs.

16. The process of claim 10 wherein the third solvent-rich stream has the same composition as that of the first solvent-rich stream.

17. The process of claim 10 wherein the solvent phase in step (d) contains solvent, benzene, water, and trace amounts of aromatic HCs.

18. The process of claim 10 wherein washing the first portion of the raffinate removes solvent.

19. The process of claim 10 wherein the sixth solvent-rich stream in step (i) contains solvent, water, and hydrocarbons and non-hydrocarbon compounds that have boiling points below that of the solvent.

* * * * *